(12) United States Patent
Clarke et al.

(10) Patent No.: US 7,651,851 B2
(45) Date of Patent: *Jan. 26, 2010

(54) HANDHELD RAMAN BODY FLUID ANALYZER

(75) Inventors: Richard H. Clarke, Big Sky, MT (US); M. Edward Womble, Austin, TX (US)

(73) Assignee: Prescient Medical, Inc., Doylestown, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/340,712

(22) Filed: Jan. 27, 2006

(65) Prior Publication Data

US 2006/0240401 A1    Oct. 26, 2006

Related U.S. Application Data

(63) Continuation-in-part of application No. 10/905,956, filed on Jan. 27, 2005, now Pat. No. 7,524,671.

(51) Int. Cl.
C12M 1/34 (2006.01)
G01J 3/44 (2006.01)

(52) U.S. Cl. .................. 435/287.1; 356/301

(58) Field of Classification Search .......... None
See application file for complete search history.

(56) References Cited

U.S. PATENT DOCUMENTS

| | | | |
|---|---|---|---|
| 3,598,727 A | 8/1971 | Willcock |
| 3,900,396 A | 8/1975 | Lamadrid |
| 4,127,033 A | 11/1978 | Warren et al. |
| 4,172,033 A | 10/1979 | Willcock |
| 4,267,040 A | 5/1981 | Schal |
| 4,329,986 A | 5/1982 | Babb |
| 4,370,983 A | 2/1983 | Lichtenstein |
| 4,573,761 A | 3/1986 | McLachlan et al. |
| 4,733,253 A | 3/1988 | Daniele |
| 4,769,134 A | 9/1988 | Allan et al. |
| 4,781,458 A | 11/1988 | Angel et al. |
| 4,913,142 A | 4/1990 | Kittrell et al. |
| 5,011,284 A | 4/1991 | Tedesco et al. |
| 5,112,127 A | 5/1992 | Carrabba et al. |
| 5,139,334 A | 8/1992 | Clarke |
| 5,199,431 A | 4/1993 | Kittrell et al. |
| 5,266,498 A | 11/1993 | Tarcha et al. |
| 5,280,788 A | 1/1994 | Janes et al. |
| 5,290,275 A | 3/1994 | Kittrell et al. |
| 5,304,173 A | 4/1994 | Kittrell et al. |
| 5,318,024 A | 6/1994 | Kittrell et al. |
| 5,372,135 A | 12/1994 | Mendelson et al. |
| 5,376,556 A | 12/1994 | Tarcha et al. |
| 5,377,004 A | 12/1994 | Owen et al. |
| 5,381,237 A | 1/1995 | Sela |
| 5,400,136 A | 3/1995 | Vo-Dinh |
| 5,419,323 A | 5/1995 | Kittrell et al. |
| 5,439,000 A | 8/1995 | Gunderson et al. |
| 5,445,972 A | 8/1995 | Tarcha et al. |
| 5,452,723 A | 9/1995 | Wu et al. |
| 5,455,673 A | 10/1995 | Alsmeyer et al. |
| 5,534,997 A | 7/1996 | Schrader et al. |
| 5,553,616 A | 9/1996 | Ham et al. |
| 5,562,100 A | 10/1996 | Kittrell et al. |
| 5,567,628 A | 10/1996 | Tarcha et al. |
| 5,615,673 A | 4/1997 | Berger et al. |
| 5,621,522 A | 4/1997 | Ewing et al. |
| 5,657,404 A | 8/1997 | Buchanan et al. |
| 5,685,988 A | 11/1997 | Malchesky |
| 5,693,043 A | 12/1997 | Kittrell et al. |
| 5,697,373 A | 12/1997 | Richards-Kortum et al. |
| 5,715,263 A | 2/1998 | Ventrudo et al. |
| 5,751,415 A | 5/1998 | Smith et al. |
| 5,773,835 A | 6/1998 | Sinofsky |
| 5,815,260 A | 9/1998 | Dou et al. |

(Continued)

FOREIGN PATENT DOCUMENTS

DE    4433305    4/1996

(Continued)

OTHER PUBLICATIONS

Bao et al. Anal Chem 2004;76(15)4531-4536.*

(Continued)

Primary Examiner—Jon P Weber
Assistant Examiner—Bin Shen
(74) Attorney, Agent, or Firm—Michele V. Frank; Patton Boggs LLP (57) ABSTRACT

Methods and apparatus for in vitro detection of an analyte in a body fluid sample using low resolution Raman spectroscopy are disclosed. The body fluid analyzer includes a disposable strip for receiving a sample of body fluid on a target region, the target region including gold sol-gel to provide surface enhanced Raman scattering. A light source irradiates the target region to produce a Raman spectrum consisting of scattered electromagnetic radiation that is separated into different wavelength components by a dispersion element. A detection array detects at least some of the wavelength components of the scattered light and provides data to a processor for processing the data. The results of the processed data are displayed on a screen to inform a user about an analyte within the body fluid sample.

25 Claims, 3 Drawing Sheets

U.S. PATENT DOCUMENTS

| | | | |
|---|---|---|---|
| 5,817,007 | A | 10/1998 | Fodgaard et al. |
| 5,842,995 | A | 12/1998 | Mahadevan-Jansen et al. |
| 5,849,179 | A | 12/1998 | Emerson et al. |
| 5,858,186 | A | 1/1999 | Glass |
| 5,862,273 | A | 1/1999 | Pelletier |
| 5,864,397 | A | 1/1999 | Vo-Dinh |
| 5,870,188 | A | 2/1999 | Ozaki et al. |
| 5,902,246 | A | 5/1999 | McHenry et al. |
| 5,902,247 | A | 5/1999 | Coe et al. |
| 5,951,482 | A | 9/1999 | Winston et al. |
| 5,982,484 | A | 11/1999 | Clarke et al. |
| 5,991,653 | A | 11/1999 | Richards-Kortum et al. |
| 5,993,378 | A | 11/1999 | Lemelson |
| 6,018,389 | A | 1/2000 | Kyle et al. |
| 6,038,887 | A | 3/2000 | Vild et al. |
| 6,044,285 | A | 3/2000 | Chaiken et al. |
| 6,064,897 | A | 5/2000 | Lindberg et al. |
| 6,087,182 | A | 7/2000 | Jeng et al. |
| 6,095,982 | A | 8/2000 | Richards-Kortum et al. |
| 6,144,444 | A | 11/2000 | Haworth et al. |
| 6,151,522 | A | 11/2000 | Alfano et al. |
| 6,154,596 | A | 11/2000 | Ionov |
| 6,156,002 | A | 12/2000 | Polaschegg et al. |
| 6,174,291 | B1 | 1/2001 | McMahon et al. |
| 6,208,887 | B1 | 3/2001 | Clarke |
| 6,212,424 | B1 | 4/2001 | Robinson |
| 6,219,137 | B1 | 4/2001 | Vo-Dinh |
| 6,226,082 | B1 | 5/2001 | Roe |
| 6,258,027 | B1 | 7/2001 | Sternby |
| 6,281,971 | B1 | 8/2001 | Allen et al. |
| 6,284,131 | B1 | 9/2001 | Hogard et al. |
| 6,284,141 | B1 | 9/2001 | Shaldon et al. |
| 6,310,686 | B1 | 10/2001 | Jiang |
| H2002 | H | 11/2001 | McLachlan et al. |
| H2202 | H | 11/2001 | McLachlan et al. |
| 6,313,914 | B1 * | 11/2001 | Roe .......................... 356/301 |
| 6,373,567 | B1 | 4/2002 | Wise et al. |
| 6,486,948 | B1 | 11/2002 | Zeng |
| 6,507,747 | B1 | 1/2003 | Gowda et al. |
| 6,511,814 | B1 | 1/2003 | Carpenter |
| 6,514,767 | B1 | 2/2003 | Natan |
| 6,560,478 | B1 | 5/2003 | Alfano et al. |
| 6,574,501 | B2 | 6/2003 | Lambert et al. |
| 6,580,935 | B1 | 6/2003 | Wach et al. |
| 6,621,574 | B1 | 9/2003 | Forney et al. |
| 6,643,012 | B2 | 11/2003 | Shen et al. |
| 6,666,840 | B1 | 12/2003 | Falkvall et al. |
| 6,690,966 | B1 | 2/2004 | Rava et al. |
| 6,721,583 | B1 | 4/2004 | Durkin et al. |
| 6,750,065 | B1 | 6/2004 | White et al. |
| 6,750,963 | B2 | 6/2004 | Sampas |
| 6,770,488 | B1 | 8/2004 | Carron et al. |
| 6,841,159 | B2 | 1/2005 | Simonson |
| 6,844,200 | B2 | 1/2005 | Brock |
| 6,897,951 | B2 | 5/2005 | Womble et al. |
| 6,924,153 | B1 | 8/2005 | Boehringer et al. |
| 7,102,746 | B2 | 9/2006 | Zhao |
| 7,245,369 | B2 | 7/2007 | Wang et al. |
| 7,326,576 | B2 | 2/2008 | Womble et al. |
| 7,351,212 | B2 | 4/2008 | Roe |
| 7,374,546 | B2 | 5/2008 | Roe et al. |
| 2003/0105069 | A1 | 6/2003 | Robinson et al. |
| 2003/0231305 | A1 | 12/2003 | Zeng |
| 2004/0116829 | A1 | 6/2004 | Raney et al. |
| 2004/0127789 | A1 | 7/2004 | Ogawa |
| 2004/0127819 | A1 | 7/2004 | Roe |
| 2004/0160601 | A1 | 8/2004 | Womble et al. |
| 2004/0174520 | A1 | 9/2004 | Premasirl et al. |
| 2004/0186394 | A1 | 9/2004 | Roe et al. |
| 2004/0191921 | A1 | 9/2004 | Farquharson et al. |
| 2004/0204634 | A1 | 10/2004 | Womble et al. |
| 2005/0059894 | A1 | 3/2005 | Zeng et al. |
| 2005/0105084 | A1 | 5/2005 | Wang et al. |
| 2005/0128476 | A1 | 6/2005 | Zhao |
| 2005/0171436 | A1 | 8/2005 | Clarke et al. |
| 2005/0250141 | A1 | 11/2005 | Lambert et al. |
| 2005/0264808 | A1 | 12/2005 | Wang |
| 2006/0166302 | A1 | 7/2006 | Clarke et al. |
| 2006/0176478 | A1 | 8/2006 | Clarke et al. |
| 2006/0240401 | A1 | 10/2006 | Clarke et al. |
| 2007/0059203 | A1 | 3/2007 | Burrell et al. |
| 2007/0224683 | A1 | 9/2007 | Clarke et al. |
| 2008/0064120 | A1 | 3/2008 | Clarke et al. |

FOREIGN PATENT DOCUMENTS

| | | |
|---|---|---|
| EP | 1846571 | 10/2007 |
| JP | 2007/553245 | 7/2007 |
| WO | WO 99/10742 | 3/1999 |
| WO | WO 2006/081380 | 8/2006 |
| WO | WO 2007/089540 | 8/2007 |
| WO | WO 2007/089551 | 8/2007 |
| WO | WO 2007/092173 | 8/2007 |

OTHER PUBLICATIONS

Goodridge, C.F., "Rapid on-site cyanide assay for blood and saliva samples", Database: Toxcenter, DN Crisp-2003-GM68246-01, 2004, Abstract.*

Hanlon E.B. et al. "Prospects for In vivo Raman spectrosoopy," Phys. Med. Biol 45 (2000) R1-R59.

Premasiri, W. Ranjith et al. "Urine Analysis by Laser Raman Spectroscopy," Lasers in Surgery and Medicine 28 (2001) pp. 330-334.

Clarke, R.H. et al. "Low-resolution Raman Spectroscopy as an Analytical Tool for Organic Liquids," Spectroscopy 13 (Oct. 1998) pp. 28-35 (downloaded on Jul. 31, 2003 from www.oceanoptics.com. products/ramanarticle.asp).

Clarke R.H. et al. "Low-Resolution Raman Spectroscopy: Instrumentation and Applications in Chemical Analysis," Journal of Raman Spectroscopy 30 (1999) pp. 827-832.

Berger, Andrew Joshua. "Measurement of analytes in human serum and whole blood samples by near-infrfed Raman spectroscopy," Ph.D. Dissertation, Massachusetts Institute of Technology, Jun. 1998.

Berger, Andrew J. et al. "Multicomponent blood analysis by near-Infrared Raman spectroscopy," Applied Optics 38:13 (May 1, 1999) pp. 2916-2926.

"RamanProbe" brochure published by InPhotonics (no publication date available).

Womble, M. Edward et al. "Low-Resolution Raman Method Offers Low Cost and Portability," Laser Focus World (Apr. 1999) pp. 131-136.

Bao et al.; Anal Chem 2004; 76(15) 4531-4536.

International Search Report dated Sep. 11, 2007 for corresponding International Application No. PCT/US07/02062.

U.S. Appl. No. 11/698,083, filed Jan. 26, 2007, Clarke et al.

International Search Report dated Sep. 11, 2007 for corresponding International Application No. PCT/US07/02062.

Berger, A. J. et al., "Feasibility of measuring blood glucose concentration by near-infrared Raman spectroscopy," Spectrochimica Acta Part A, 1997; 53:287-292.

Berger, A. J. et al., "Rapid, noninvasive concentration measurements of aqueous biological analytes by near-infrared Raman spectroscopy," Applied Optics, 1996, 35(1):209-212.

Brennan, J. F. et al., "Histochemical Analysis of Human Coronary Artery Using Near-Infrared Raman Spectroscopy," Proc. Of SPIE; 1994; 2324:98-102.

Kneipp, K. et al., "Near-infrared surface-enhanced Raman scattering (NIR-SERS) of neurotransmitters in colloidal silver solutions," Spectrochimica Acta, 1995; 51(A)(3): 481-487.

Liistro, F. et al., "First Clinical Experience With a Paclitaxel Derivate-Eluting Polymer Stent System Implantation for In-Stent Restenosis: Immediate and Long-Term Clinical and Angiographic Outcome," Circulation, 2002; 105, 1883-1886.

Morice, M. et al., "A Randomized Comparison of a Sirolimus-Eluting Stent with a Standard Stent for Coronary Revascularization," N. Engl. J. Med., 2002; 346(23):1773-1780.

Sharma, S. et al., Correction "Sirolimus-Eluting Coronary Stents," N. Engl. J. Med., 2002; 347:1285.

Nave, S.E., "Rugged Fiber Optic Probes and Sampling Systems for Remote Chemical Analysis Via the Raman Technique," Advances in Instrumentation and Control, 1996; 51:453-467.

Qu. J. Y. et al, "Rapid quantification of the clinically important analytes in sub-µl simulating human sera," Proc. of SPIE, 2000, 3918:174-180.

Römer, T. J. et al., "Histopathology of Human Coronary Atherosclerosis by Quantifying Its Chemical Composition with Raman Spectroscopy," Cirulation 1998; 97:878-885.

Schultz, C. P. et al, "A Comparison of Non-destructive and Non-invasive material depth profiling using FT-Raman fiber optics and microspectroscopy," Proc. Of SPIE, 2000; 4129:284-293.

Serruys, P.W. et al., "Intravascular Ultrasound Findings in the Multicenter, Randomized, Double-Blind RAVEL (Randomized study with the sirolimus-eluting Velocity balloon-expandable stent in the treatment of patients with de novo native coronary artery Lesions) Trial," Circulation, 2002, 106:798-803.

Shim, M.G. et al, "Evaluation of fiber optic probes for in vivo Raman spectroscopy," SPIE, 1998; 3257:208-217.

Walker, P.A. III et al., "Capillary isotachophoresis with fiber-optic Raman spectroscopic detection Performance and application to ribonucleotides," Journal of Chromatography A, 1998; 805:269-275.

Williams, K.P.J., "Remote Sampling Using a Fibre-Optic Probe in Fourier Transform Raman Spectroscopy," Journal of Raman Spectroscopy, 1990; 21: 147-151.

Zimba, C.G. et al., "FT-Raman Spectroscopy with Fiber-Optic Probes and a Diode-Bar-Pumped Nd:YAG Laser," Applied Spectroscopy, 1991; 45(2): 162-165.

International Search Report, PCT/US2007/002106, dated Apr. 7, 2008.

International Search Report, PCT/US2007/002108, dated Nov. 20, 2007.

* cited by examiner

HANDHELD RAMAN BODY FLUID ANALYZER

This application is a continuation-in-part of and claims priority to U.S. patent application Ser. No. 10/905,956 filed Jan. 27, 2005 (now U.S. Pat. No. 7,524,671).

BACKGROUND OF THE INVENTION

The present invention generally relates to methods and apparatus for testing biological samples, and in particular, to systems for in vitro testing of body fluid samples for analytes, such as glucose.

The ability to monitor an analyte within a blood sample has greatly improved the diagnosis and treatment of diseases such as diabetes. For example, home monitors allow diabetics to test glucose levels by pricking their finger and applying a small sample of blood to a test strip. Based on the glucose reading, diet and/or insulin dosage can be adjusted.

Generally, these home glucose monitor systems use an electrochemical detection technique based on glucose oxidase reactions. The system can include a disposable strip having electrodes and the glucose oxidase enzyme. When a blood drop is applied to the target area of the electrode, the glucose oxidase catalyzes the oxidation of glucose in the drop to produce gluconic acid. During the reaction, electrons are transferred by an electrochemical mediator to the electrode surface. This in turn generates a current that is measured by the sensor. The amount of current generated is proportional to the amount of glucose present in the blood drop, thus giving an accurate reading of the blood glucose concentration.

While the ease of use and the low cost of these home monitor systems have proven helpful for regular blood sugar monitoring, they are limited by the amount of information that can be provided using a glucose oxidase reaction. Information on other substances within the blood is not readily available without incorporation of additional reagents and assays.

Spectroscopic approaches to glucose monitoring have also been suggested. In one such approach, laser light is directed through or into a portion of a patient's skin and reflectance or scattered light is captured by a detector. A spectroscopic measurement of the blood glucose level is then obtained from the detected light. This method has met with limited success because of the cost, complexity, and difficulty of transdermal monitoring.

For these reasons, there continues to exist a need in this art for better devices and methods for testing blood and other body fluid samples.

SUMMARY OF THE INVENTION

The present invention provides methods and apparatus for in vitro detection of analytes in a body fluid sample using Raman spectroscopy, such as low resolution Raman spectroscopy. The apparatus may, for example, be a low-resolution Raman spectroscopy system that employs a multimode laser source for radiating a sample and producing a Raman spectrum consisting of scattered electromagnetic radiation. The radiation is then separated into different wavelength components by a low resolution dispersion element and detected by a detection array. Data from the array is processed by a processor to provide information about one or more analytes.

In one aspect of the invention, the handheld Raman analyzer can provide information about multiple analytes. For example, the analytes can include glucose plus at least one additional analyte selected from the group consisting of insulin, hemoglobin, cholesterol, electrolytes, antioxidants, nutrients, and other body fluid components. Other analytes that can be detected and/or monitored with the present invention include, but are not limited to, drugs such as therapeutic drugs (prescription or over-the-counter) or drugs of abuse (such as illicit drugs), metabolites of drugs (such as therapeutic drugs or drugs of abuse), alcohol, poisons, disease markers and other body fluid components.

In another aspect, a system is disclosed including a disposable test strip that provides surface enhanced Raman Scattering (SERS). In one embodiment, the test strip can include a metallic surface or a surface that includes metallic (e.g., silver or gold) particles. One embodiment is a test strip with a sample-receiving region that includes gold nanoparticles stabilized in a porous sol-gel silicate.

In another aspect, the present invention includes a method for analyzing body fluid samples including providing a disposable strip for receiving a sample of body fluid on a target region and depositing the sample on the target region of the disposable strip. The target area is then irradiated with a laser to produce a Raman spectrum consisting of scattered electromagnetic radiation which is separated into different wavelength components using a low resolution dispersion element. At least some of the wavelength components are detected using a detection array and the resulting data is processed by a processor to asses an analyte within the body fluid sample. Results from the processor may optionally be displayed on a screen.

BRIEF DESCRIPTION OF THE DRAWINGS

The invention will be more fully understood from the following detailed description taken in conjunction with the accompanying drawings.

DETAILED DESCRIPTION OF THE INVENTION

The present invention generally relates to a system for in vitro detection of one or more analytes in a body fluid sample, such as blood, urine or saliva, using Raman spectroscopy, such as low resolution Raman spectroscopy. The system may include a disposable strip for receiving a sample of body fluid on a target region and a laser for irradiating the target region to produce a Raman spectrum consisting of scattered electromagnetic radiation. For low-resolution Raman spectroscopy, a low resolution dispersion element, positioned to receive the scattered radiation, preferably separates the radiation into different wavelength components, and at least some of the wavelength components are then detected by a detection array. Data from the detection array is passed to a processor for processing the data to evaluate an analyte within the body fluid sample. The system can also evaluate multiple analytes within the body fluid sample.

While conventional glucose monitors have improved home monitoring of blood glucose levels, such electrochemical devices fail to inform the user about other important substances within the blood. Testing of other analytes can be performed in medical laboratories, but at significant time and expense. The present invention overcomes these drawbacks by using Raman spectroscopy, such as low resolution Raman spectroscopy, in a handheld device, to detect analytes within a body fluid sample. The handheld device of the present invention provides a cost efficient method for testing multiple analytes in a single sample.

Figure 1:
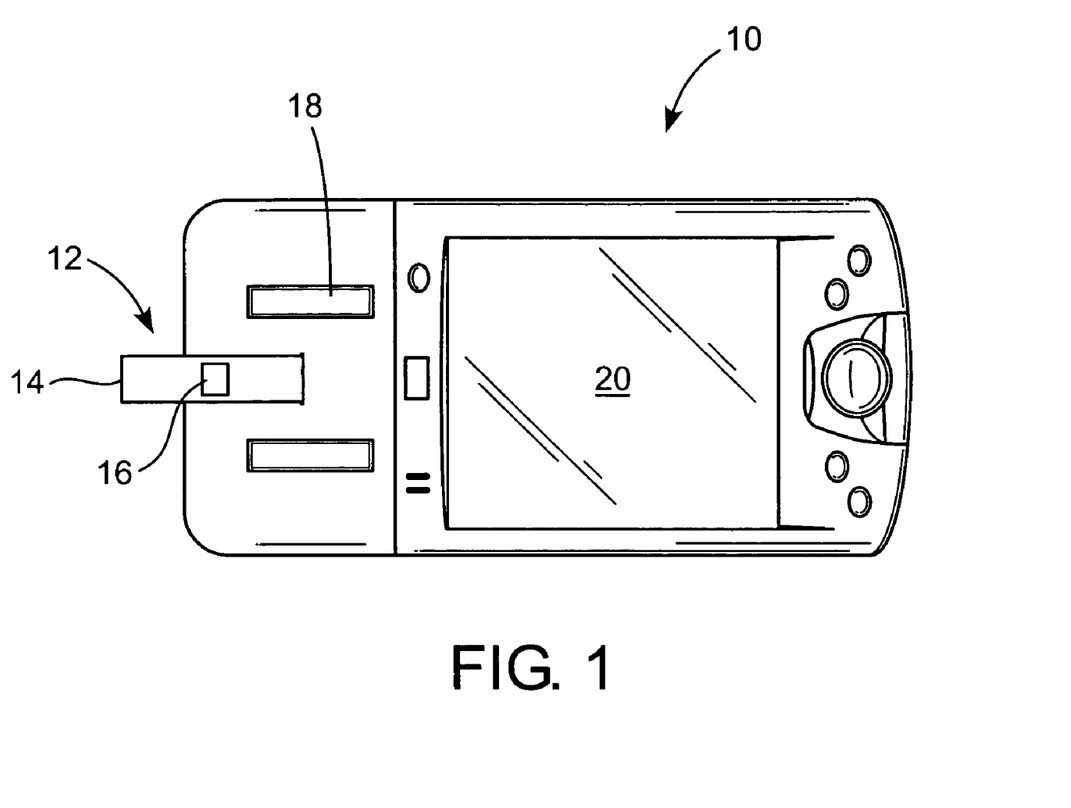
FIG. 1 is a top view of a handheld Raman body fluid analyzer according to the present invention.

FIG. 1 illustrates one embodiment of the handheld Raman device 10 of the present invention including a sampling area 12 containing a target area 16, on test strip 14, for receiving a body fluid sample. Spectroscopic components 18, preferably positioned within device 10, produce radiation and provide spectroscopic measurements of the body fluid sample. Results from the spectroscopic analysis can be shown on screen 20.

Figure 2:
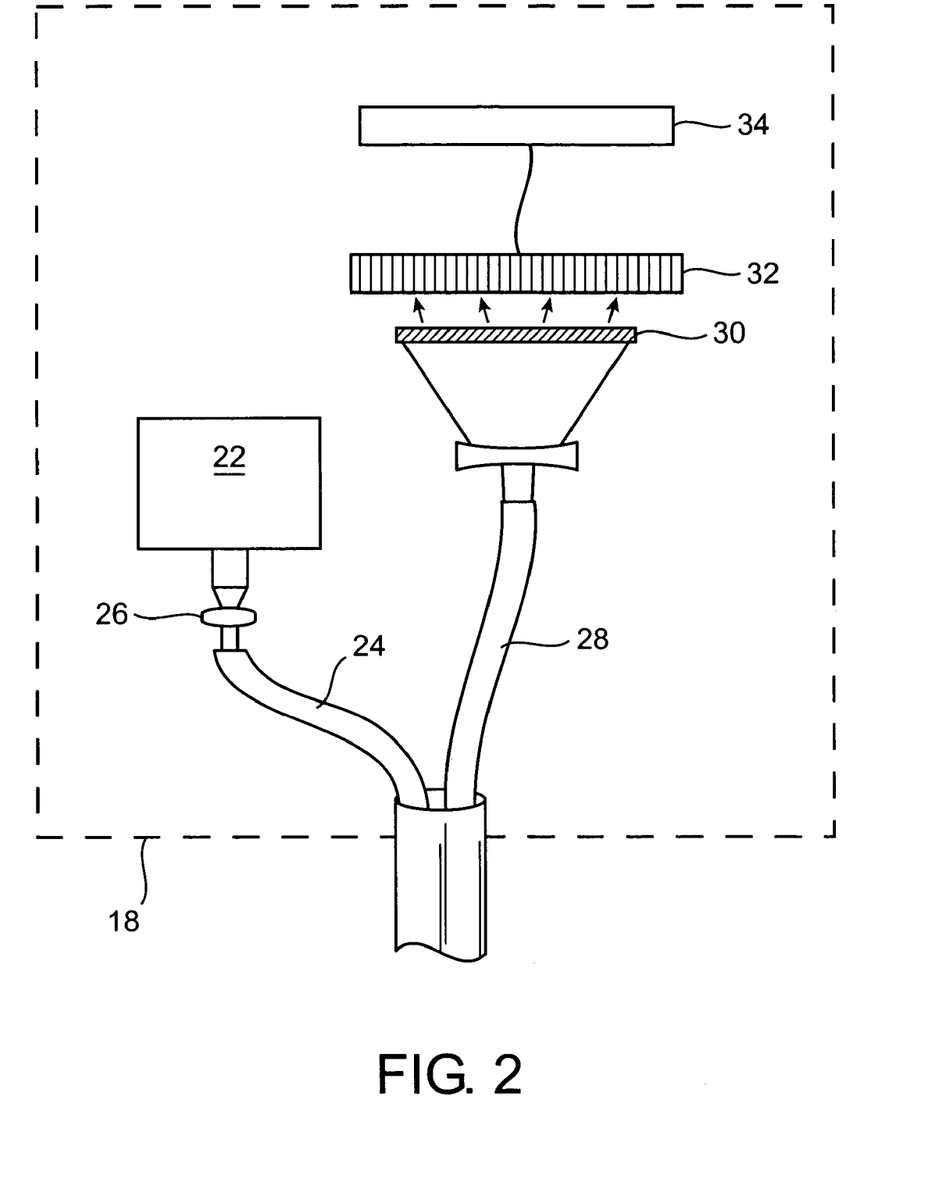
FIG. 2 is a schematic illustration of another embodiment of the present invention.

A more detailed example of spectroscopic components 18 is provided in FIG. 2, which shows a low-resolution Raman spectroscopy apparatus that includes a multi-mode laser source 22 and optical fiber 24 connected to the laser source for carrying laser light to the sampling site. Relay optics 26 can optionally be used with the optical fiber to focus and direct the radiation. A person skilled in the art will appreciate that optical fiber 24 may include a variety of optical fibers and light carrying materials that can collect and direct radiation.

Light is preferably directed by optical fiber 24 to the sampling area 12, and after encountering the body fluid sample, is returned in a second optical fiber 28. The returned radiation is directed through dispersion element 30 that serves to disperse the scattered light into different wavelength components. The dispersed scattered light is detected by photodetector array 32 that, in this case, consists of a photodiode array or a charged-coupled device (CCD) array. The signals generated by detector array 32 in response to the scattered light are then sent to a microprocessor 34 for analysis.

The present invention allows specific spectral bands of interest to be measured at low resolution to obtain the integrated band intensities. These bands can be narrow ones. The resolving power of the dispersion device 30 determines the position of specific wavelengths in the diode array in such a way that the signal from a particular diode in the array will typically correspond to the same (or a similar) narrow range of wavelengths. This combination of the low-resolution dispersion device 30 and the diode array photodetector 32 thus form a spectrometer. The microprocessor 34 selects a particular diode (or diodes) of the array 32 according to the property to be measured. The integrated signals lying in the two ranges can be arithmetically divided to form intensity ratios. The microprocessor 34 compares these ratios with known values or a correlating function to obtain an estimate of the chemical constituent or property of interest. In addition, the microprocessor can analyze multiple analytes within a single sample in a single test. In one embodiment, the procedure is repeated for a second analyte by choosing the appropriate diode(s) for the additional analyte. The processor can also run these calculations in series using stored information from the diodes.

The terms "radiation", "laser" and "light" are herein utilized interchangeably. In particular, the term "light" can refer to radiation having wavelength components that lie in the visible range of the electromagnetic spectrum, or outside the visible range, e.g., the infrared or ultraviolet range of the electromagnetic spectrum. In certain embodiments of Raman spectroscopy, the preferred excitation wavelengths will range from about 700 nanometers to 2.5 micrometers. Although this portion of the electromagnetic spectrum is commonly known as infrared (IR) radiation, the term "light" will be used as a shorthand expression in describing the path of this radiation as well as the various wavelengths of radiation induced by Raman scattering and collected for analysis.

Advances in the field of solid-state lasers have introduced several important laser sources into Raman analysis. For high-resolution Raman systems the laser linewidth must be severely controlled, often adding to the cost of the excitation source and the system as a whole. For low resolution Raman spectroscopy (LRRS), however, the strategy of relinquishing resolution details in favor of emphasizing essential identifying spectral features, allows the use of a low cost, high energy multi-mode laser and a low resolution dispersion element. A multi-mode laser which can be used with a LRRS system, according to one embodiment of the present invention, is available in higher power ranges (between 50 mw and 1000 mw) than is available with a traditional single mode laser (<150 milliwatts). The higher power of a multi-mode laser increases the amount of scattered radiation available to the spectrometer system and the sensitivity of the LRRS system increases at least linearly with laser power.

A low resolution dispersion element can provide greater transmission of scattered radiation to the detector array. For example, a low resolution diffraction grating with wider slits than a typical diffraction grating can be used, providing greater transmission of incident scattered radiation to the detector array. Thus, the combination of a low cost, high energy multi-mode laser and a low loss dispersion element provides an inexpensive LRRS system with a high intensity signal.

In a typical LRRS application the need for feature separation is much like that encountered in mid-IR spectroscopy. The use of multi-mode lasers causes degradation in the resolution of the spectrometer. The resolution of the LRRS system decreases primarily because the width of the laser line used to excite the sample is much larger with multi-mode lasers than it is with a single mode laser. A multi-mode laser may have a linewidth of about 2-3 nanometers, generally on the order of one or more nanometers. In comparison, a single mode laser has a linewidth of a fraction of a nanometer. However, one rarely requires single wavenumber resolution to find a spectral fingerprint feature that allows identification and quantification of a sample under analysis. Similarly, in LRRS, since the approach uses fundamental frequencies, even if not fully resolved, in the spectral analysis, a broader band laser source may suffice for the Raman analysis. In this case inexpensive, multi-mode solid-state laser sources are both sufficient for the task and provide cost effective high power.

Since a Raman measurement is the difference in wavelength between the scattered light and the excitation line, an excitation line that has a larger spectral FWHM causes a proportional loss of resolution in the resulting Raman measurement. However, this reduction of resolution is offset by the advantages of lower cost and increased signal intensity. The increased signal intensity is a result of a higher energy laser source and wider slits in the diffraction grating allowing more light into the detector array. Since the spectrometer system resolution has been substantially reduced by the use of a multi-mode laser, the width of the slits can be increased with a negligible effect on resolution. In addition, a CCD detector array can be matched to the lower resolution laser source and the dispersion element by reducing the number of elements in the array. For example, instead of 4096 array elements, one can use 2048 larger elements.

Thus, a complete LRRS spectroscopic system can consist of an inexpensive multi-mode laser diode operating at a higher power (between 50 mw and 1000 mw output) than traditional single-mode Raman sources and a low resolution monochromator matched to a simple CCD detector, with Rayleigh filtering provided by edge or notch filters capable of removing the excitation source background.

Various multi-mode laser components can be used with the device of the present invention. For example, the B&W Tek multi-mode laser BWF-OEM-785-0.5, available from B&W Tek, Inc., of Newark, Del., can be used as the multi-mode laser. The optical fibers utilized in the present invention apparatus of the invention are preferably multimode fibers, which are available from several commercial sources including, for example, Fiberguide, Inc. of Sterling, N.J. Their diameters may range from 1 µm to 1000 µm, preferably from about 100 µm to about 400 µm, and more preferably from about 100 µm to about 200 µm. Single fibers and fiber bundles can also be utilized in the present invention. In addition, various low resolution monochromators can be used as detector arrays. For example, Ocean Optics S-1000 and S-2000 monochromators are commercially available from Ocean Optics of Dunedin, Fla. Optical filters can be used to eliminate the Rayleigh line.

The microprocessor used with the device of the present invention can include any computer with sufficient storage capacity and processing capability to house a library of body fluid components for matching and quantifying. An exemplary microprocessor is the Compaq iPAQ from the Hewlett-Packard Company.

The device of the present invention can include a number of other features that can assist with analyzing samples in the sampling area. In one embodiment, sampling area 12 includes an optical assembly 40 as illustrated schematically in FIG. 3. Optical assembly 40 directs the light received from spectroscopic components 18 into position for contacting the sample, collects the scattered radiation, and returns the collected radiation for analysis.

Figure 3:
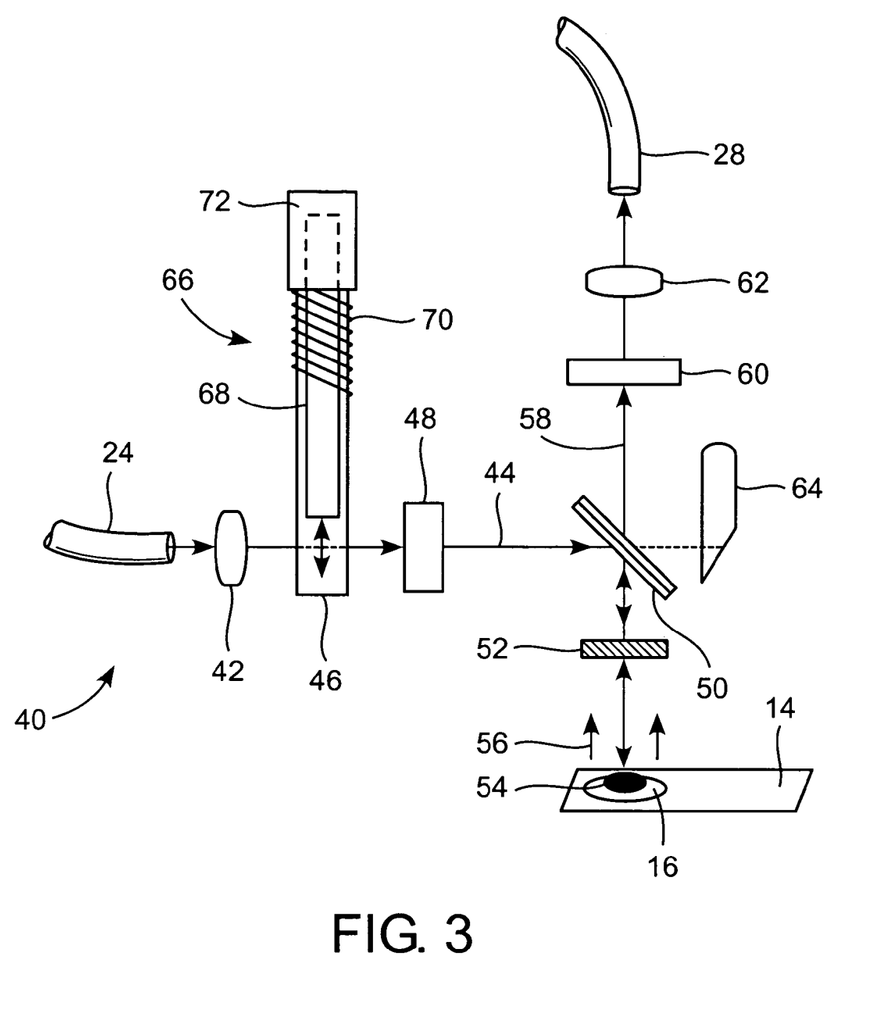
FIG. 3 is a schematic illustration of yet another embodiment of the present invention.

Excitation radiation enters optical assembly 40 via optical fiber 24. The beam from the input fiber is passed through lens 42, which serves to collimate or otherwise project the incoming radiation along beam path 44 with minimal dispersion. The radiation from lens 42 then passes through an optional safety switch including chamber 46 and through one or more optional filters 48, e.g., a low-pass filter.

The filtered incoming light is then reflected by dichroic beam-splitter 50 (which is designed to reflect nearly all of the excitation light) and directed toward target area 16. A second lens 52 can be disposed to focus the excitation radiation to a particular point or region within a sample 54. Preferably, lens 52 focuses the light on target area 16.

Returning radiation 56 passes through lens 52, which now serves to collimate the scattered radiation and convey it to collection fiber 28. From lens 52, the collected radiation travels along beam path 58, passing through dichroic beam-splitter 50 and, optionally, a mid-pass or long-pass filter 60 and lens 62. Lens 62 serves to focus the collected radiation into output fiber 28. (It should be appreciated that the lens elements of the present invention can be simple or compound lens assemblies and that the functions that these optical elements perform—directing excitation radiation into a sample and collecting scattered radiation for analysis—can be achieved by various equivalent structures, such as those known to ones skilled in the art.)

Optical assembly 40 can further include a "beam dump" 64 to capture and absorb incoming radiation that is not reflected by dichroic beam-splitter 50. Beam dump 64 can comprise a chamber that has been coated with suitable radiation absorbing material or otherwise formed or shaped to ensure that the radiation that is not directed into the sampling tube is captured and dissipated as heat.

Safety switch 66 is formed by a protective shutter, as shown in FIG. 3, that is disposed in chamber 46. Chamber 46 intersects incoming beam path 44. Plunger 68 is disposed within chamber 46 and operatively connected to spring 70 and solenoid 72. In an activated state, solenoid 72 pulls plunger 68 out of light beam path 44, thereby allowing the multimode radiation to pass through optical assembly 40 and to sample 54. In a deactivated state, ("laser blocking" position), the solenoid releases plunger 68, which moves into light beam path 44 and prevents the multimode radiation from passing to the outside environment. Thus, safety switch 66 ensures that the probe remains in a "normally-off" state should a malfunction or power loss occur.

The handheld Raman device of the present invention can additionally include a disposable test strip 14. Test strip 14, pictured in FIG. 1, preferably provides an area to deposit a body fluid sample onto which the laser radiation is directed, and even more preferably, includes features to enhance spectroscopy. In one embodiment, the test strip can include a substance for surface enhanced Raman spectroscopy (SERS), such as a roughened metallic surface and/or SERS-active metallic particles. The SERS-active metallic particles may, for example, be solid metallic particles or particles that are at least partially coated with a SERS-active metal.

SERS techniques enhance Raman spectroscopic signals and allow more effective differentiation of spectroscopic signatures by placing the sample to be analyzed in contact with SERS material (usually an appropriately prepared metal surface). Two mechanisms are considered responsible for the improvement. The primary contribution is an enlargement of the local electromagnetic field, due to the excitation of a localized surface plasmon, while the other mechanism results from a charge transfer-state between the surface complex of the adsorbed molecule and the metal surface.

Figure 4:
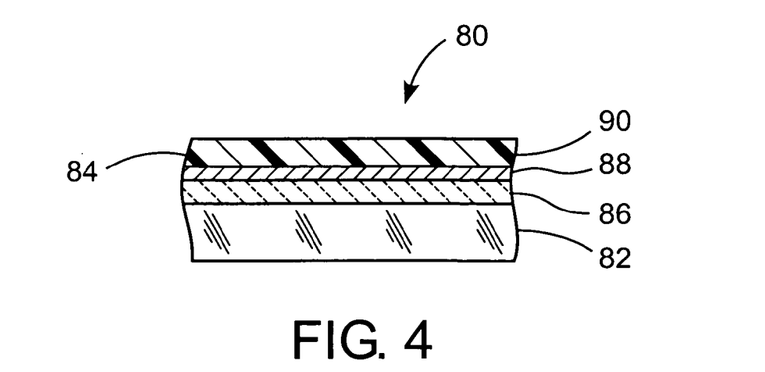
FIG. 4 is a test strip of the present invention including a surface enhanced Raman spectrometry material.

Preferably, a SERS test strip includes SERS-active material, such as, for example silver, gold, nickel, copper and/or cadmium. FIG. 4 illustrates one exemplary embodiment of SERS active test strip 80 including a support substrate 82 and a roughened metal surface layer 84 having a degree of roughness sufficient to induce the SERS effect. Layer 84 may include a microparticle or microstructure layer 86 on the upper surface of support substrate 82 and a metal layer 88 containing silver, gold, nickel, copper and/or cadmium.

In one embodiment, a coating 90 can be applied to roughened surface layer 84 to sorb analytes which are not easily adsorbed by the roughened surface and which are capable of either penetrating into the coating or being attached to the coating. The analytes are thereby "adsorbed" and become positioned in the vicinity of the roughened surface and exhibit the SERS effect.

In one embodiment, the SERS active material is positioned only in target area 16 of the test strip. In use, a sample is deposited on the SERS-active material in the target area and light is directed toward the sample for spectroscopic analysis. A person of skill in the art will appreciate that the choice of SERS-active material will depend on the desired analyte and the chosen radiation spectrum. In one embodiment, the SERS-active materials include a porous sol-gel containing gold microcollooid particles where the laser radiation is about 785 nm. SERS techniques and materials are described in U.S. Pat. Nos. 5,400,136 and 5,864,397 to Vo-Dinh, which are incorporated herein by reference in their entirety.

In one embodiment, the device of the present invention additionally includes a lancet, which can puncture a user's skin, typically on the user's finger, to draw a blood sample. The lancet preferably includes a sharpened tip and a mechanism for propelling the metal tip into a user's skin. An exemplary lancet is the BD Ultra-Fine™ Lancet available from BD Consumer Healthcare, Ontario, Canada.

Where the device of the present invention investigates multiple analytes within a single sample during a single analysis it may be particularly advantageous to test analytes related to a single condition of interest. For example, when a patient arrives for a check-up, instead of running two diagnostic tests related to one condition, e.g., one for blood sugar, one for hemoglobin A1c, the present invention allows simultaneous testing. The result is a cost effective and almost immediate analysis. Thus, one embodiment of the invention provides for the analysis of multiple analytes that are related to a single preselected condition or to the health status of a preselected organ or tissue system.

Other groups of analytes can include a blood chemistry profile (a test for levels of two or more of: urea, creatinine, uric acid, bilirubin, phosphorous, alkaline P-Tase, total protein, albumin, globulin, glucose, calcium, calcium ionized, magnesium, iron, sodium, potassium, chloride, carbon dioxide, T-3 uptake, T-4 RIA, free thyroxine index, TSH-ultra sensitive cholesterol, triglycerides, HDL, LDL, VLDL, iron, iron saturation, and ferritin).

In another embodiment, mineral and heavy metal assessments may be desirable to reveal the levels of beneficial elements and toxic elements that commonly occur in humans as the result of lifestyle and toxic exposures. Preferred analytes include mercury, iron, calcium, phosphorous, magnesium, and lead. Such a test may be desirable for persons concerned with health hazards in their living or work space.

In yet another embodiment, analytes may be chosen which focus on a certain preselected health condition. For example, testing for analytes related to cardiac health may be desirable during a regular check-up or as part of a heart health screening. Such analytes may, for example, include two or more of cholesterol (total, LDL, HDL), triglycerides, C-reactive protein, and homocysteine.

In an additional embodiment, it may be desirable to screen for a group of drugs, and in particular illegal drugs or drugs of abuse, such as but not limited to narcotics, amphetamines and hallucinogens. As an example, analytes could include two or more of marijuana (including but not limited to active substance THC), amphetamines, barbiturates, methamphetamines, opioids (such as but not limited to morphine, heroin and synthetic opioids), and PCP.

The Raman methods and apparatuses of the invention may be used to monitor pharmacotherapy in human or animal subjects. The quantification of a preselected drug and/or its metabolites in a sample obtained from a patient may be used to determine whether the active species of the drug is/are present at a desired concentration in the patient, and if not, the cause of the problem. The activity of many therapeutic drugs is at least partially dependent on their metabolism to one or more active forms within the body. For example, buproprion (Zyban™, Wellbutrin™) is extensively metabolized into three active metabolites. Activity of the antihypertensive angiotensin I-converting enzyme (ACE) inhibitors benazepril, enalapril, moexipril, and quinapril is due to the active metabolites benazeprilat, enalaprilat, moexiprilat, and quinaprilat, respectively. The antihistamine terfenadine is metabolized to an active metabolite fexofenadine. Determining the relative concentration of parent drug to active metabolite(s) in a patient, according to the invention, provides an indication of whether drug metabolism is normal and/or whether an abnormality in metabolism that interferes with the pharmacotherapy may be present, for example due to a metabolic insufficiency in the patient. Determining the concentration(s) of parent drug and/or metabolites thereof in a patient can provide information as to whether there is a problem in drug absorption/administration or a patient's compliance therewith, if the desired level of drug or metabolites is not achieved.

One embodiment of the invention provides a method for monitoring pharmacotherapy of a subject that includes the steps of: obtaining a sample of a body fluid, such as blood, urine or saliva, from a subject; irradiating at least a portion of the sample with monochromatic light to produce a Raman spectrum consisting of scattered electromagnetic radiation; detecting at least some of the wavelength components of the Raman spectrum that are associated with a preselected drug, such as a therapeutic drug, and/or one or more metabolites of the drug; and determining the concentration of the drug and/or one or more metabolites in the body fluid based on the detected wavelength components. In one variation, the subject has previously received the drug via a route of administration at least once. Another variation of the embodiment includes the further steps of: detecting at least some of the wavelength components of the Raman spectrum for one or more analytes that are associated with the state of a condition treated by the drug; and determining the concentration of the one or more analytes in the body fluid based on the detected wavelength components of the Raman spectrum for the one or more analytes. A test strip apparatus as described herein may, for example, be used to implement the embodiment and its variations.

The present invention provides the ability to monitor a variety of analytes using a test simple enough for use at home and sophisticated enough to provide valuable information about select analytes.

The results determined by the processor can be displayed on screen 20. Depending on the particulars of the analyte and the user's needs, the displayed results can be provided in a variety of forms. For example, where glucose is tested, the results can be displayed quantitively (120 mg/dl) or relatively (Normal). With other analytes, it may be desirable to display results indicating only the presence (or absence) of an analyte (e.g., the presence of poisons).

The term "body fluid" as used herein includes, but is not limited to, blood, urine and saliva. Other body fluids include, for example, lymph and cerebrospinal fluid.

General background information on Raman spectral analysis can be found in U.S. Pat. No. 5,139,334, issued to Clarke and incorporated herein by reference in its entirety, which teaches a low resolution Raman analysis system for determining certain properties related to hydrocarbon content of fluids. The system utilizes a Raman spectroscopic measurement of the hydrocarbon bands and relates specific band patters to the property of interest. See also, U.S. Pat. No. 6,208,887 also issued to Clarke and incorporated herein by reference in its entirety, which teaches a low-resolution Raman spectral analysis system for determining properties related to in vivo detection of samples based on a change in the Raman scattered radiation produced in the presence or absence of a lesion in a lumen of a subject. Additionally, U.S. application Ser. No. 10/367,238 (U.S. Pub. No. 20040160601) entitled "Probe Assemblies for Raman Spectroscopy" describes devices for analyzing samples with Raman spectroscopy and is incorporated herein by reference in its entirety. U.S. Pub. No. 20040174520 entitled "Low resolution surface enhanced Raman spectroscopy on sol-gel substrates," U.S. Pub. No. 20040204634 entitled "Raman spectroscopic monitoring of hemodialysis," and U.S. Pub. No. 20050171436 entitled "Raman spectroscopy for monitoring drug-eluting medical devices" are each also incorporated by reference herein in their entireties.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

The invention claimed is:

1. An apparatus for in vitro detection of an analyte in a body fluid sample using low resolution Raman spectroscopy with a resolution of between 10 cm$^{-1}$ and 100 cm$^{-1}$ comprising:
   a disposable strip for receiving a sample of body fluid on the target region;
   a light source for irradiating the target region to produce a Raman spectrum consisting of scattered electromagnetic radiation;
   a low resolution diffraction grating dispersion element positioned to receive and separate the scattered radiation into different wavelength components;
   a detection array, optically aligned with the dispersion element for detecting at least some of the wavelength components of the scattered light; and
   a processor for processing data from the detector array and calculating information about an analyte within the body fluid sample.

2. The apparatus of claim 1, wherein the processor calculates information about multiple analytes within the body fluid sample.

3. The apparatus of claim 2, wherein the multiple analytes further comprise at least one body fluid component.

4. The apparatus of claim 2, wherein the multiple analytes further comprise at least one drug.

5. The apparatus of claim 2, wherein the multiple analytes further comprise at least one disease marker.

6. The apparatus of claim 2, wherein the multiple analytes further comprise at least one poison.

7. The apparatus of claim 2, wherein the multiple analytes comprise at least two analytes related to a single preselected condition.

8. The apparatus of claim 7, wherein the single preselected condition is a single preselected health condition.

9. The apparatus of claim 2, wherein the multiple analytes comprise at least two analytes related to cardiac health.

10. The apparatus of claim 1, wherein the concentration of the analyte within the body fluid sample is calculated.

11. The apparatus of claim 1, wherein the disposable strip comprises a SERS-active material.

12. The apparatus of claim 11, wherein the disposable strip comprises a gold sol-gel strip to provide surface-enhanced Raman scattering.

13. The apparatus of claim 1, wherein the light source is a multi-mode laser.

14. The apparatus of claim 1, wherein the processor comprises a library of spectral properties of analytes for comparing with spectral information obtained from the body fluid sample.

15. The apparatus of claim 14, wherein the test strip target region comprises gold.

16. The apparatus of claim 14, wherein the test strip target region comprises a sol-gel.

17. The apparatus of claim 1, further comprising a screen for displaying information related to the analyte detected within the body fluid sample.

18. The apparatus of claim 17, wherein the at least one other analyte comprises hemoglobin A1c.

19. The apparatus of claim 1, wherein the analyte is selected from the group consisting of urea-based compounds, ammonium-based compounds, uric acid based compounds, nitrogen-based compounds, and combinations thereof.

20. The apparatus of claim 1, wherein the detected analyte in the body fluid sample is selected from the group consisting of cardiac enzymes, cardiovascular stent coatings, poisons, therapeutic drugs, drugs of abuse, hormones, steroids, and combinations thereof.

21. The apparatus of claim 1, further comprising a lancet to puncture a patient's skin.

22. The apparatus of claim 1, wherein the analyte is a therapeutic drug.

23. The apparatus of claim 1, wherein the analyte is a metabolite of a therapeutic drug.

24. The apparatus of claim 2, wherein the multiple analytes comprise a therapeutic drug and one or more metabolites of the drug.

25. An apparatus for in vitro detection of an analyte in a body fluid sample using low resolution Raman spectroscopy with a resolution of between 10 cm$^{-1}$ and 100 cm$^{-1}$ comprising:
   a test strip for receiving a sample of body fluid on a target region, the target region comprising a metallic material to provide surface enhanced Raman scattering;
   a laser for irradiating the target region to produce a Raman spectrum consisting of scattered electromagnetic radiation;
   a low resolution diffraction grating dispersion element positioned to receive and separate the scattered radiation into different wavelength components;
   a detection array, optically aligned with the dispersion element for detecting at least some of the wavelength components of the scattered light; and
   a processor for processing data from the detector array and calculating glucose concentration and information about at least one other analyte within the body fluid sample.

* * * * *